United States Patent
Chen et al.

(10) Patent No.: US 11,452,435 B2
(45) Date of Patent: Sep. 27, 2022

(54) DEFLECTION DEVICE OF STEERABLE ENDOSCOPE

(71) Applicant: Issa Technology Co., Ltd., Taoyuan (TW)

(72) Inventors: Yung-Yun Chen, Taoyuan (TW); Chi-Wei Chiu, Taoyuan (TW)

(73) Assignee: ISSA TECHNOLOGY CO., LTD., Taoyuan (TW)

( * ) Notice: Subject to any disclaimer, the term of this patent is extended or adjusted under 35 U.S.C. 154(b) by 574 days.

(21) Appl. No.: 16/382,296

(22) Filed: Apr. 12, 2019

(65) Prior Publication Data
US 2019/0320882 A1 Oct. 24, 2019

(30) Foreign Application Priority Data

Apr. 18, 2018 (TW) ................................ 107113128

(51) Int. Cl.
*A61B 1/005* (2006.01)
*A61M 25/01* (2006.01)

(52) U.S. Cl.
CPC .......... *A61B 1/0055* (2013.01); *A61B 1/0051* (2013.01); *A61B 1/0057* (2013.01); *A61B 1/0058* (2013.01); *A61M 25/0147* (2013.01)

(58) Field of Classification Search
CPC ..... A61B 1/005; A61B 1/0051; A61B 1/0052; A61B 1/0053; A61B 1/0055; A61B 1/0056; A61B 1/0057; A61B 1/0058; A61B 1/008; A61B 2017/003; A61B 2017/00305; A61B 2017/00309; A61B 2017/00314; A61B 2017/00318; A61B 2017/00323; A61M 25/0133; A61M 25/0136; A61M 25/0141; A61M 25/0144; A61M 25/0147; A61M 25/0152; A61M 25/0155; A61M 25/0158
See application file for complete search history.

(56) References Cited

U.S. PATENT DOCUMENTS

| | | | |
|---|---|---|---|
| 6,447,478 B1 * | 9/2002 | Maynard | F03G 7/065 604/95.05 |
| 8,398,587 B2 * | 3/2013 | Dewaele | A61B 34/70 600/101 |
| 9,579,013 B2 * | 2/2017 | Dewaele | A61B 1/00071 |
| 9,669,204 B2 * | 6/2017 | Suehara | A61M 25/0147 |
| 10,449,010 B2 * | 10/2019 | Dewaele | A61B 1/0055 |
| 10,596,363 B2 * | 3/2020 | Suehara | A61M 25/0138 |

(Continued)

*Primary Examiner* — Ryan N Henderson
(74) *Attorney, Agent, or Firm* — McClure, Qualey & Rodack, LLP

(57) ABSTRACT

A deflection device of steerable endoscope includes a first base, a second base, elastic reposition members and tendon wires. The second base is located above the first base along the endoscope center axis. The elastic reposition members are inlaid between the first and the second bases. Each elastic reposition member includes a first plate connecting to the first base, a second plate connecting to the second base, and a waveform bar connecting the first and the second plates. The wave-height of the waveform bar is not parallel to the endoscope center axis. The tendon wires are located on the two opposite sides of each elastic reposition member. The tendon wires are parallel to and distant from the endoscope center axis. Bending of the steerable endoscope is precisely controlled, and structure of the deflection device is simplified in the invention.

9 Claims, 8 Drawing Sheets

(56) References Cited

U.S. PATENT DOCUMENTS

| | | | |
|---|---|---|---|
| 11,109,745 B2* | 9/2021 | Matthison-Hansen | ........................ A61B 1/0056 |
| 2008/0194911 A1* | 8/2008 | Lee | ........................ A61B 1/042 600/109 |
| 2009/0069632 A1* | 3/2009 | McIntyre | .............. A61B 1/0055 600/146 |
| 2011/0004157 A1* | 1/2011 | Dewaele | ............... A61B 1/0055 604/95.01 |
| 2011/0034764 A1* | 2/2011 | Verbeek | ............ A61M 25/0138 600/101 |
| 2013/0253481 A1* | 9/2013 | Dewaele | ............ A61M 25/0158 606/1 |
| 2014/0207173 A1* | 7/2014 | Su | ........................... A61B 1/005 606/1 |
| 2016/0015249 A1* | 1/2016 | Suehara | ............ A61M 25/0138 604/95.04 |
| 2016/0015250 A1* | 1/2016 | Suehara | ............ A61M 25/0147 604/95.04 |
| 2016/0015251 A1* | 1/2016 | Suehara | ............ A61M 25/0147 604/95.04 |
| 2017/0172678 A1* | 6/2017 | Dewaele | ............ A61M 25/0141 |
| 2017/0232233 A1* | 8/2017 | Suehara | .................... A61B 1/04 604/95.04 |
| 2019/0231169 A1* | 8/2019 | Thissen | .............. A61M 25/0054 |
| 2020/0275983 A1* | 9/2020 | Dewaele | .............. A61B 1/0055 |

* cited by examiner

DEFLECTION DEVICE OF STEERABLE ENDOSCOPE

CROSS REFERENCE TO RELATED APPLICATIONS

This Non-provisional application claims priority under 35 U.S.C. § 119(a) on Patent Application No. 107113128 filed in Taiwan on Apr. 18, 2018, the entire contents of which are hereby incorporated by reference.

BACKGROUND

1. Technical Field

The invention relates to a deflection device of steerable endoscope, in particular, to a deflection device of steerable endoscope driven by shape memory alloys (SMA).

2. Description of Related Art

The development of endoscope technology is mainly to enable the observation of environments that are inaccessible to human beings or living things. In order to easily visit various environments or observe images in various directions, a steerable endoscope structure has been developed, which makes the endoscope lens have the function of deflection. The flexible structure of the endoscope is usually a combination of a ring metal and rivets or uses a spring as a flexible component, which is controlled by two tendon wires and a motor. Therefore, the endoscope has the function of bidirectional deflection to control the direction of the lens of the endoscope.

However, there are still some problems to be overcome in the use of the deflection device of the endoscope. Firstly, the conventional deflection device of endoscope consists of various components such as ring metal, rivet holes, rivets, spring, tendon wires and motor. Because endoscope technology requires the overall size of the device to be extremely small, the large number of parts will lead to much higher precision of each component. It not only makes the production process more complicated, but also greatly increases the manufacturing and assembly costs, which is not conducive to the popularization of technology due to the high price. On the other hand, if the manufacturing and assembling technology cannot satisfy the precision requirements, the conventional endoscope will be large in size and inconvenient to use.

Secondly, for deflection device of steerable endoscope adopting spring, the elasticity of the spring and the tendon wires is easy to fatigue and fracture, and the control degree of the bending direction is not satisfactory, thus affecting the operation of the deflection device. The ability of this deflection device of steerable endoscope to control the direction is low, or additional direction-control components are often required, resulting in higher costs.

Thirdly, for deflection device of steerable endoscope adopting ring metal, the turning angle is limited and fixed due to the limitation of ring metal structure, which cannot reach a wide range of turning angle and cannot fully observe the environment image, resulting in image omission.

Therefore, it is an important subjective to provide a deflection device of steerable endoscope to improve the above deficiencies.

SUMMARY OF THE INVENTION

In view of the foregoing, one of the objects of the present invention is to provide a deflection device of steerable endoscope, which can precisely control lens steering and consists of fewer components.

For the above objects, a deflection device of steerable endoscope includes a first base, a second base, a plurality of elastic reposition members and a plurality of tendon wires. The second base is positioned above the first base along the direction of endoscope central axis and the elastic reposition members are inlaid between the first base and the second base. Each elastic reposition member includes a first plate, a second plate and a waveform bar. The first plate is connected to the first base while the second plate to the second base. The waveform bar is connected between the first plate and the second plate, the wave-height direction of which is not parallel to the direction of the central axis of the endoscope. The tendon wires are arranged on the two opposite sides of each elastic reposition member. The tendon wires are parallel to and distant from the endoscope central axis.

In one embodiment, the first base has a plurality of first clamp parts and the second base has a plurality of second clamp parts. Every first plate has a third clamp part and each second plate has a fourth clamp part. The third clamp part coordinates with the first clamp part to connect the first plate to the first base while the fourth clamp part cooperates with the second clamp part to connect the second plate to the second base.

In summary, the deflection device of steerable endoscope adopts elastic reposition members with a waveform bars and shape memory alloy tendon wires to drive the steering. It can precisely control the bending operation of endoscope, simplify the structure of deflection device, apply to small-size endoscope, and reduce the manufacturing cost.

The detailed technology and preferred embodiments implemented for the subject invention are described in the following paragraphs accompanying the appended drawings for people skilled in this field to well appreciate the features of the claimed invention.

BRIEF DESCRIPTION OF THE DRAWINGS

The parts in the drawings are not necessarily drawn to scale, the emphasis instead being placed upon clearly illustrating the principles of at least one embodiment. In the drawings, like reference numerals designate corresponding parts throughout the various diagrams, and all the diagrams are schematic.

DETAILED DESCRIPTION

Reference will now be made to the drawings to describe various inventive embodiments of the present disclosure in detail, wherein like numerals refer to like elements throughout.

Figure 1:
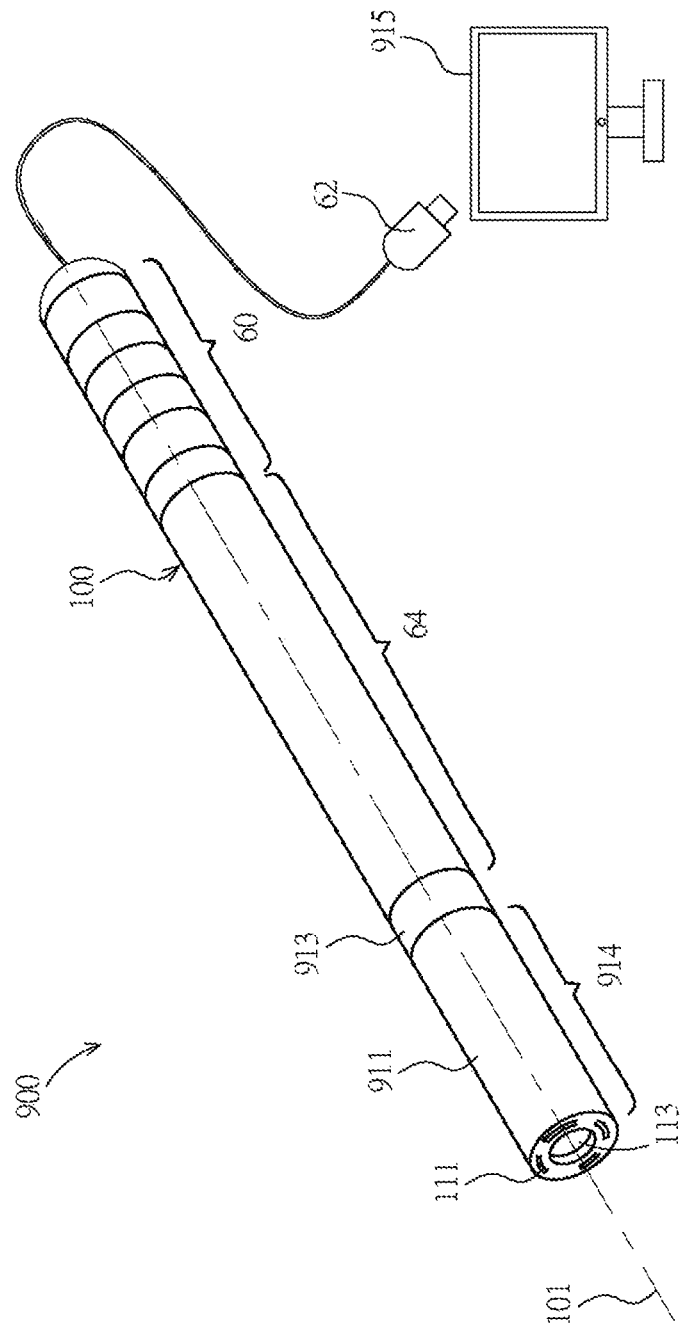
FIG. 1 is a schematic diagram showing the structure of a deflection device of steerable endoscope according to a first embodiment of the invention.

FIG. 1 is a schematic diagram showing the structure of a steerable endoscope 900 according to the first embodiment of the invention. As shown in FIG. 1, the steerable endoscope 900 includes a deflection device of steerable endoscope 100, a tube 911, a light emitting module 913, an image capture module 914 and a connector 62.

The image capture module 914 is positioned at one end (front end) of the steerable endoscope 900 for capturing target images, such as images inside a human body or images inside a device. The image capture module 914 includes image sensors such as charge-coupled device (CCD) or complementary metal oxide semiconductors (CMOS). The light emitting module 913, for example including LED or Organic LED (OLED) light sources, provides the light required for the image capture module 914. The light source of the light emitting module 913 may be arranged behind the image capture module 914 and can make use of the opening 111 or the light guide components to guide light to the front end of the steerable endoscope 900 (but not limited to that). The function of the tube 911 is to contain the deflection device of steerable endoscope 100, the light emitting module 913 and the image capture module 914. There are holes 113 on the tube at the front end of the steerable endoscope 900, which is used for the image capture module 914 to capture light of the image. The material of the tube 911 may be metal, plastic, silica gel, stainless steel, plastic steel or a combination thereof.

The deflection device of steerable endoscope 100 may include a control unit 60 and a bending section 64, the latter can be bent toward multiple directions and angles. In the steerable endoscope 900 of the present invention, the bending range of the deflection device of steerable endoscope 100 can be freely controlled within an included angle range of 30° to 90° with the endoscope central axis 101. The control unit 60, including electronic devices, can control the bending operation of the deflection device of steerable endoscope 100, as well as the operation of the image capture module 914 and the light emitting module 913. The connector 62 is positioned at the other end (rear end) of the steerable endoscope 900 to be used to electrically connect to an external device 915, such as a displayer or a computer.

It is to be noted that the tube 911 wrapping the bending section 64 of the deflection device of steerable endoscope 100 must be a flexible structure, so as to satisfy the bending of the deflection device of steerable endoscope 100, but its structure and material are not limited by this embodiment. While the tube 911 covering the control unit 60 of the deflection device of steerable endoscope 100 can be a handheld part operated by an operator.

Figure 2:
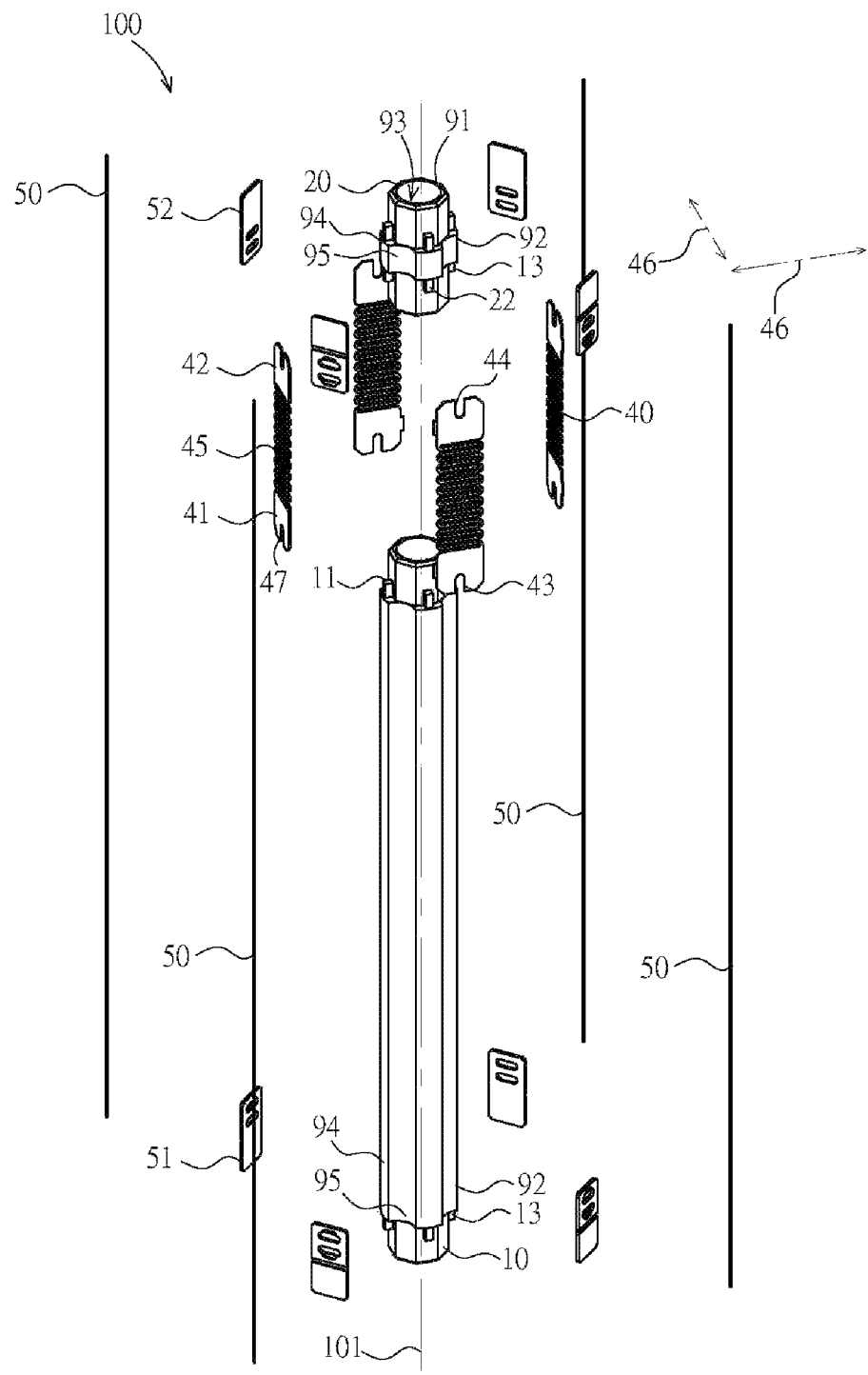
FIG. 2 is an exploded view showing a schematic structure of the deflection device of steerable endoscope according to the first embodiment of the invention.
Figure 3:
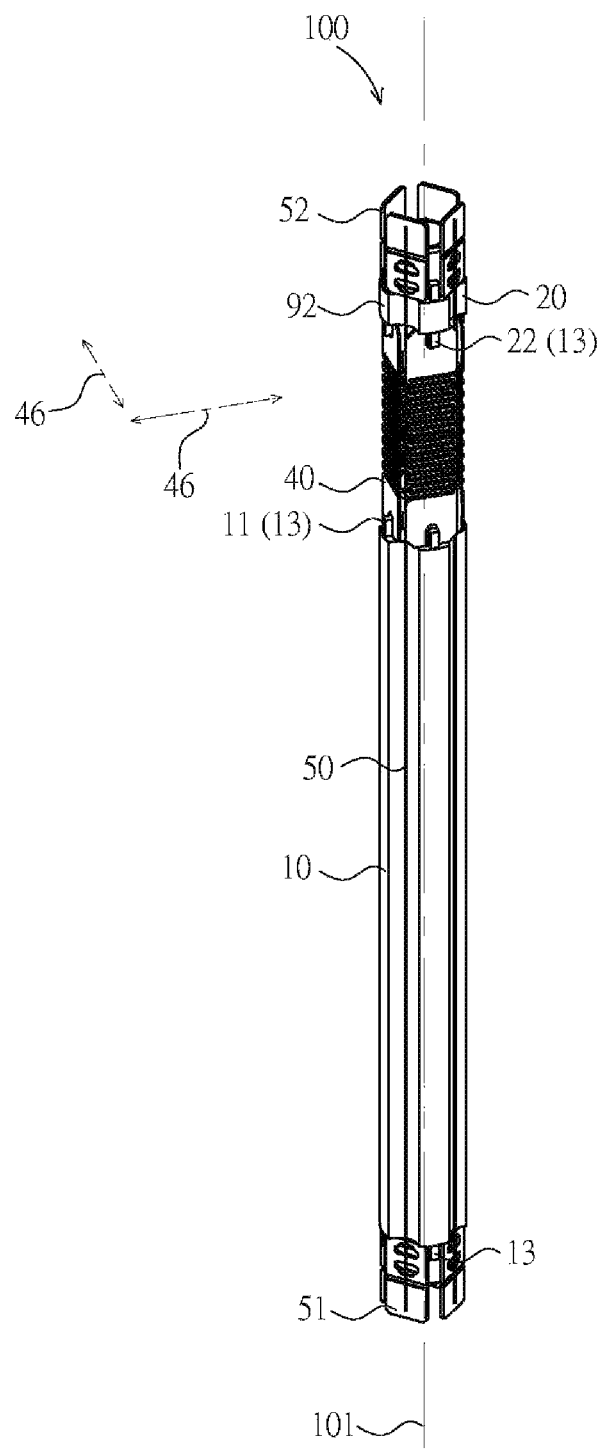
FIG. 3 is a schematic diagram showing the appearance of the deflection device of steerable endoscope according to the first embodiment of the invention.
Figure 4:
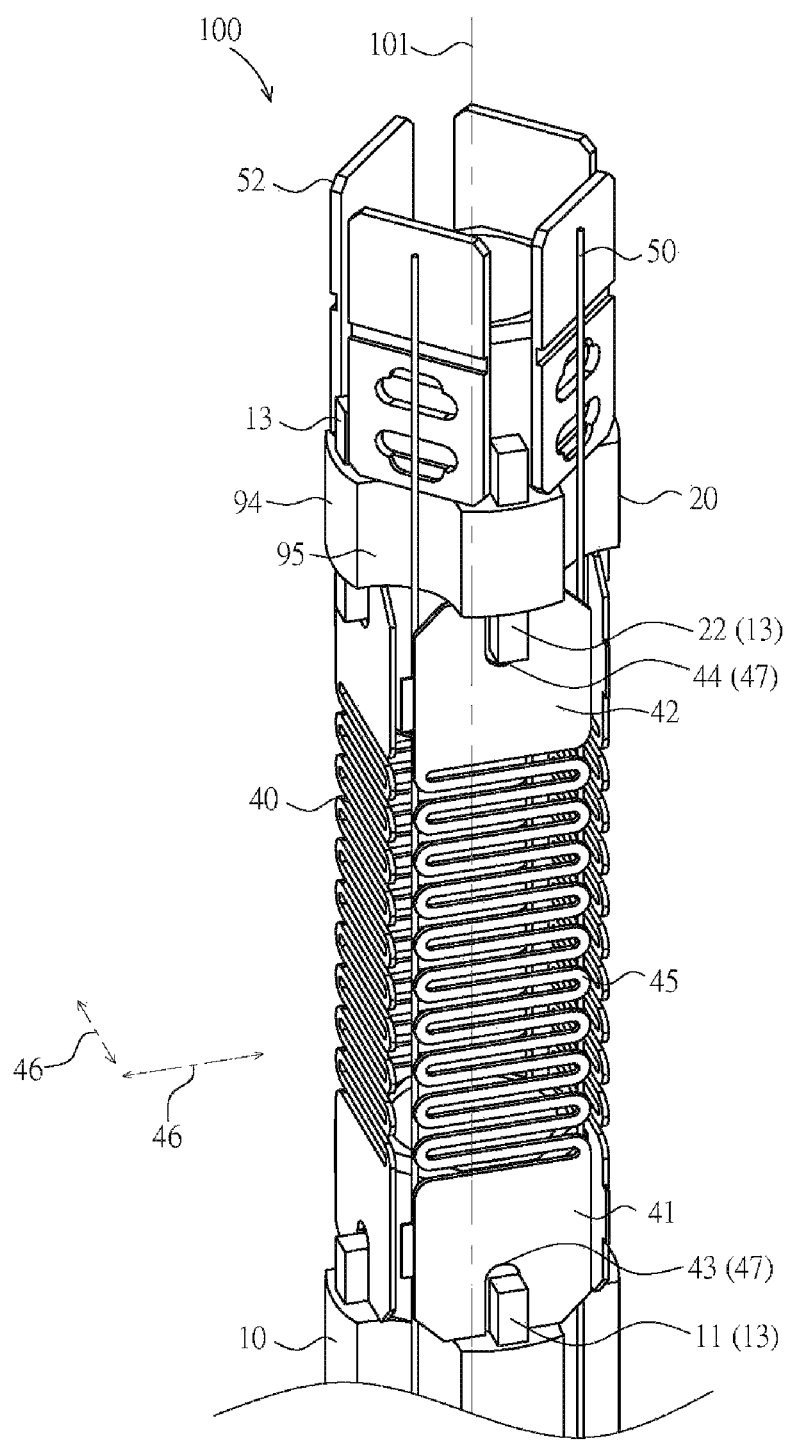
FIG. 4 is an enlarged schematic view showing a portion of the deflection device of steerable endoscope according to the first embodiment of the invention.

Please furtherly refer to FIGS. 2 to 4 for the detailed structure of the deflection device of steerable endoscope 100, which show an explosion schematic diagram, an appearance schematic diagram and an enlarged components schematic diagram of the deflection device of steerable endoscope 100 according to the first embodiment of the invention, respectively. As shown in FIGS. 2 to 4, the deflection device of steerable endoscope 100 includes one first base 10, one second base 20, four elastic reposition members 40, four tendon wires 50, four first terminal components 51 and four second terminal components 52.

In the embodiment, the first base 10 is a long strip base that can be arranged in the control unit 60 of FIG. 1. More specifically, the first base 10 approximately includes an octagonal cylinder 91, a jagged ring band 92 and eight protruding ribs 13. The cylinder center axis of the octagonal cylinder 91 is virtually located on the endoscope center axis 101, and at the center of the octagonal cylinder 91 in the first base 10 is an accommodation space 93, which penetrates through the octagonal cylinder 91 for cables and tendon wires to pass through. In the embodiment, the accommodation space 93 is a cylindrical space, and the central axis of which is virtually positioned on the endoscope central axis 101 (but not limited to that).

The jagged ring band 92 surrounds the outer surface of the octagonal cylinder 91 and there are gaps near both of the two ends of the octagonal cylinder 91. The surfaces of the jagged ring band 92 corresponding to four intervals of the octagonal cylinder 91 are protruding structures 94, while the surfaces of the jagged ring band 92 corresponding to other four intervals of the octagonal cylinder 91 are groove structures 95, which allow tendon wires 50 to pass through.

The eight protruding ribs 13 of the first base 10 are virtually parallel to the direction of the endoscope central axis 101. Four of the protruding ribs 13 extend upward from the upper surface of the protruding structure 94 of the jagged ring band 92 and act as the four first clamp part 11 of the first base 10. The other four protruding ribs 13 extend downward from the lower surface of the protruding structure 94 of the jagged ring band 92.

The second base 20 is positioned above the first base 10 along the direction of the endoscope central axis 101. The second base 20 of the embodiment hereof is a short base that can be arranged in the bending section 64 of FIG. 1. More specifically, the structure and configuration of the second base 20 are approximately the same as that of the first base 10. The main difference between the two bases is that the octagonal cylinder 91 and the jagged ring band 92 of the second base 20 are shorter than those of the first base 10 (along the direction of the endoscope central axis 101), and the four second clamp part 22 of the second base 20 are four protruding ribs 13 extending downward from the lower surface of the protruding structure 94 of the jagged ring band 92.

Every elastic reposition members 40 of the embodiment hereof is embedded between the first base 10 and the second base 20. Every elastic reposition members 40 is roughly a long thin plate and is parallel to the endoscope central axis 101, and there is a radial gap between them. Four elastic reposition members 40 are perpendicular to each other to form four side walls of a hollow square cylinder. More specifically, every elastic reposition members 40 includes a first plate 41, a waveform bar 45 and a second plate 42 from bottom to top.

There are grooves 47 on each first plate 41 and each second plate 42. The grooves 47 of the first plate 41 and the second plate 42 of each elastic reposition members 40 are respectively located at the two ends of the elastic reposition members 40, so that the first plate 41 and the second plate 42 form two C-shaped plates with outward notches. The groove 47 of the first plate 41 and the groove 47 of the second plate 42 are respectively the third clamp part 43 of the first plate 41 and the fourth clamp part 44 of the second plate 42. The shape of the third clamp part 43 is cooperated with the first clamp part 11 to connect the first plate 41 to the first base 10, while the shape of the fourth clamp part 44 is cooperated with the second clamp part 22 to connect the second plate 42 to the second base 20.

The waveform bar 45 is connected between each first plate 41 and each second plate 42, which is also called an S-shaped elastic structure. The wave-height direction 46 of each waveform bar 45 is not virtually parallel to the direction of the endoscope central axis 101. For example, the wave-height direction 46 of each waveform bar 45 is virtually perpendicular to the direction of the endoscope central axis 101, i.e. the waveform heading direction of the waveform bar 45 is parallel to the direction of the endoscope central axis 101 (but not limited to that). Specifically, the waveform bar 45 of the embodiment hereof includes 20 C-shaped bars and 19 long straight bars, which are connected to each other in a staggered order, and the C-shaped bars of the two ends are respectively linked to the first plate 41 and the second plate 42.

The four first terminal components 51 are linked to the first base 10 and are respectively located below the four groove structures 95 of the jagged ring band 92 of the first base 10, spanning and leaning against the lower surfaces of the adjacent two protruding structures 94 on both sides. On the other hand, the four second terminal components 52 are connected to the second base 20 and are respectively located above the four groove structures 95 of the jagged ring band 92 of the second base 20, spanning and leaning against the upper surfaces of the adjacent two protruding structures 94 on both sides. It is to be noted, the four first terminal components 51 may be electrically connected to each other to connected to ground. In other embodiments, the four second terminal components 52 may be electrically connected to each other to connected to ground. In other words, the four first terminal components 51 or the four second terminal components 52 may be integrated forming by a single metal plate.

The tendon wires 50, arranged on the two opposite sides of each elastic reposition members 40, are parallel to and distant from the endoscope central axis 101. Therefore, when the four elastic reposition members 40 are perpendicular to each other to form the four side walls of the hollow square cylinder, the four tendon wires 50 are approximately positioned at four corners of the hollow square cylinder. Both ends of each tendon wires 50 are respectively fixed and electrically connected to the first terminal component 51 and the second terminal component 52 (for example, connected and fixed by press of metal plates). The present invention uses the tendon wires 50 to provide the pulling force required for bending in the endoscope. Because the tendon wires 50 is fixed to the second terminal component 52 and the latter is fixed to the second base 20, the pulling force rendered by the tendon wires 50 can drive the deflection device of steerable endoscope 100 to bend.

The tendon wires 50 of the embodiment hereof includes a shape memory alloy and is electrically connected to the control unit 60, which controls contraction and stretch of the tendon wires 50 by current. After the current is cut off, the endoscope is reset by using the waveform bar as elastic force. The operation of the deflection device of steerable endoscope 100 is described below. When the control unit 60 applies current to the first terminal component 51 and the second terminal component 52 on both sides of the corresponding elastic reposition members 40, the tendon wires 50 on both sides of the corresponding elastic reposition members 40 generates a contraction force according to the received current and forces the second base 20 and the second terminal component 52 to bend toward the elastic reposition members 40. When the control unit 60 stops applying current, the elastic force of the elastic reposition members 40 can drive the deflection device of steerable endoscope 100 to return to its original position. Conversely, when the control unit 60 applies current to the first terminal component 51 and the second terminal component 52 on both sides of the opposite elastic reposition members 40, the contraction force of the opposite tendon wires 50 drives the elastic reposition members 40 to bend toward the opposite direction.

The embodiment hereof is described with the shape memory alloy tendon wires 50 as an example, which is characterized with simplifying the structure and operation of the deflection device of steerable endoscope 100. The control unit 60 of the embodiment hereof can easily control the bending and reposition of the deflection device of steerable endoscope 100 by using the current, the shape memory alloy tendon wires 50 and the elastic reposition members 40 with the waveform bar 45, so that complicated ring metal, rivet holes, rivets, springs, motors are not required (but not limited to the present invention). In other embodiments, the tendon wires 50 of the present invention may be other metals, plastics or fibers. At this time, both ends of each tendon wire 50 are respectively fixed to the first terminal component 51 and the second terminal component 52, but are not electrically connected. The control unit 60 generates the pulling force required for bending the deflection device of steerable endoscope 100 by mechanical means, for example, by pulling the tendon wires 50 with a micro motor.

Because the elastic reposition members of the present invention has waveform bar, and two sides of each elastic reposition member are respectively matched with a tendon wire for deflection and driving, the bending direction and degree of the endoscope can be conveniently and accurately controlled. Firstly, since this embodiment has elastic reposition members of four directions, when the user wants to bend the deflection device of steerable endoscope 100 in these four directions (the four directions are operated in accordance with the control habits of the common user), the user only needs to operate in the above-mentioned manner. The deflection device of steerable endoscope 100 is less likely to deflect to other directions due to the traction by the elastic reposition members and the tendon wires structure, so it has higher directional accuracy. That is, the deflection device of steerable endoscope 100 is easily bent toward four mutually perpendicular directions, and the four mutually perpendicular directions are virtually perpendicular to the direction of the endoscope central axis 101. In other words, the four bending directions of the deflection device of steerable endoscope 100 and the two extending directions of the endoscope central axis 101 essentially constitute six spatial axis directions of the 3D space.

Secondly, the present invention can actually provide a bending direction of 360°. When a user wants the deflection device of steerable endoscope 100 to bend in a direction other than the above direction, the control unit 60 only needs to apply different currents to the first terminal component 51 and the second terminal component 52 on both sides of the corresponding elastic reposition members 40 to adjust the direction, with the advantage of easily and accurately controlling the bending direction and angle.

The above embodiment is illustrated by taking a single-segment bending mechanism as an example, while other embodiments of the present invention may also have a multi-segment bending mechanism. Please refer to FIGS. 5 to 7, which show an explosion schematic diagram, an appearance schematic diagram and an enlarged components schematic diagram of the deflection device of steerable endoscope 200 according to the second embodiment of the present invention, respectively. The main difference between the second embodiment and the first embodiment is that the second embodiment has a double-segment bending mechanism. In the first good embodiment, four elastic reposition members 40 are inlaid between the first base 10 and the second base 20 to form a single-segment bending mechanism. While in the second good embodiment, in addition to that, another four elastic reposition members 40 are inlaid between the second base 20 and the third base 30 to form a double-segment bending mechanism.

Figure 5:
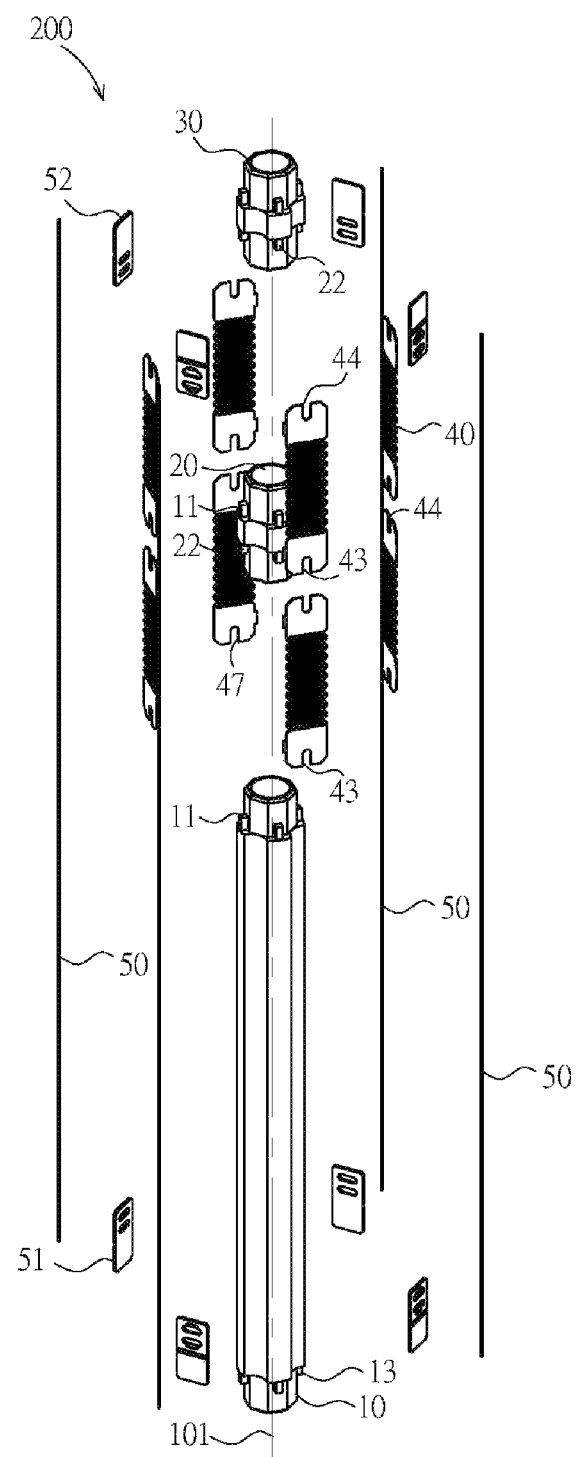
FIG. 5 is an exploded view showing a schematic structure of the deflection device of steerable endoscope according to a second embodiment of the invention.
Figure 6:
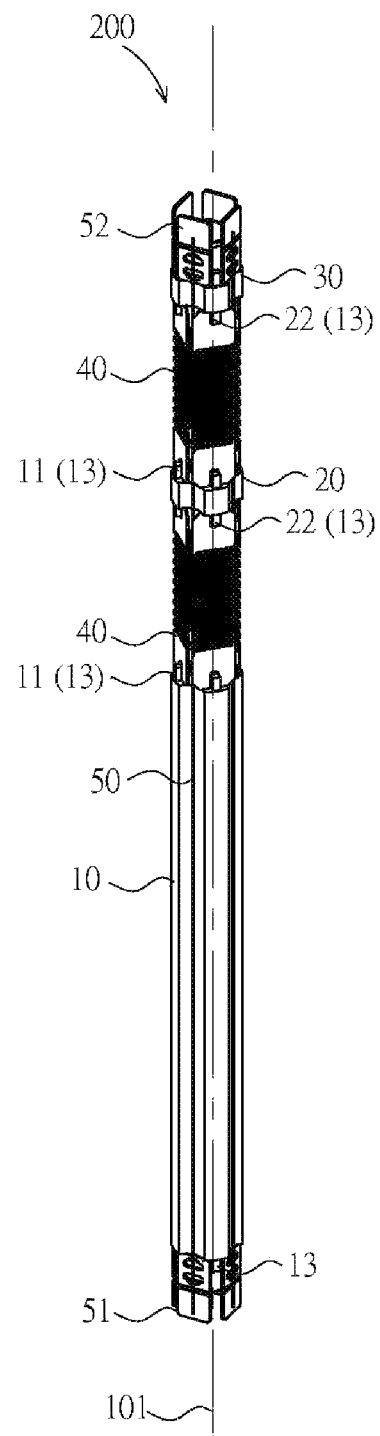
FIG. 6 is a schematic diagram showing the appearance of the deflection device of steerable endoscope according to the second embodiment of the invention.
Figure 7:
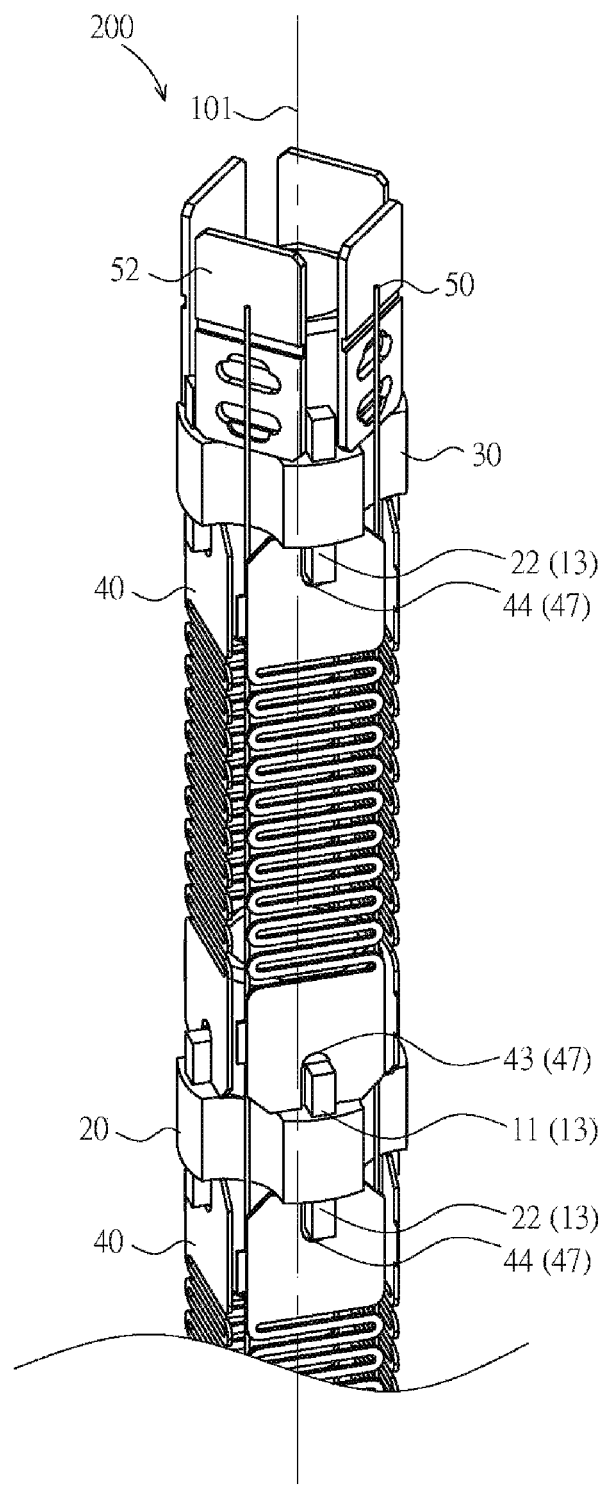
FIG. 7 is an enlarged schematic view showing a portion of the deflection device of steerable endoscope according to the second embodiment of the invention.

As shown in FIGS. 5 to 7, the deflection device of steerable endoscope 200 includes a first base 10, a second base 20, a third base 30, eight elastic reposition members 40, four tendon wires 50, four first terminal components 51 and four second terminal components 52. The third base 30, which has the same structure as the second base 20, is located above the second base 20 along the direction of the endoscope central axis 101. The previous four elastic reposition members 40 are still inlaid between the second base 20 and the first base 10, while the other four elastic reposition members 40 are embedded between the third base 30 and the second base 20.

At this time, the four second terminal components 52 are instead linked to the third base 30, while the tendon wires 50 extend upward from the first base 10, across the second base 20, and to the third base 30. The upward extending protruding ribs 13 of the first base 10 and the second base 20 act as the first clamp part 11, while the downward extending protruding ribs 13 of the second base 20 and the third base 30 act as the second clamp part 22. The shape of the first clamp part 11 is matched with the groove 47 of the third clamp part 43, and the shape of the second clamp part 22 is matched with the groove 47 of the fourth clamp part 44.

The four elastic reposition members 40 located between the first base 10 and the second base 20 can be used as the first-segment bending mechanism, while another four elastic reposition members 40 located between the second base 20 and the third base 30 can be used as the second-segment bending mechanism. In contrast to a single-segment bending mechanism, the deflection device of steerable endoscope 200 with the double-segment bending mechanism can provide a larger range of bending angle. For example, if each segment of bending mechanism has a bending angle of 30°, a deflection device of steerable endoscope with a single-segment bending mechanism can provide a largest bending angle of 30°. The deflection device of steerable endoscope 200 with a double-segment bending mechanism can provide a bending angle of 60°, and can be suitable for applications requiring large deflection angle. The above angles are only examples and are not limiting to the invention. Moreover, the present invention can provide more bending mechanisms in other embodiments by just increasing the number of bases and elastic reposition members 40.

Figure 8:
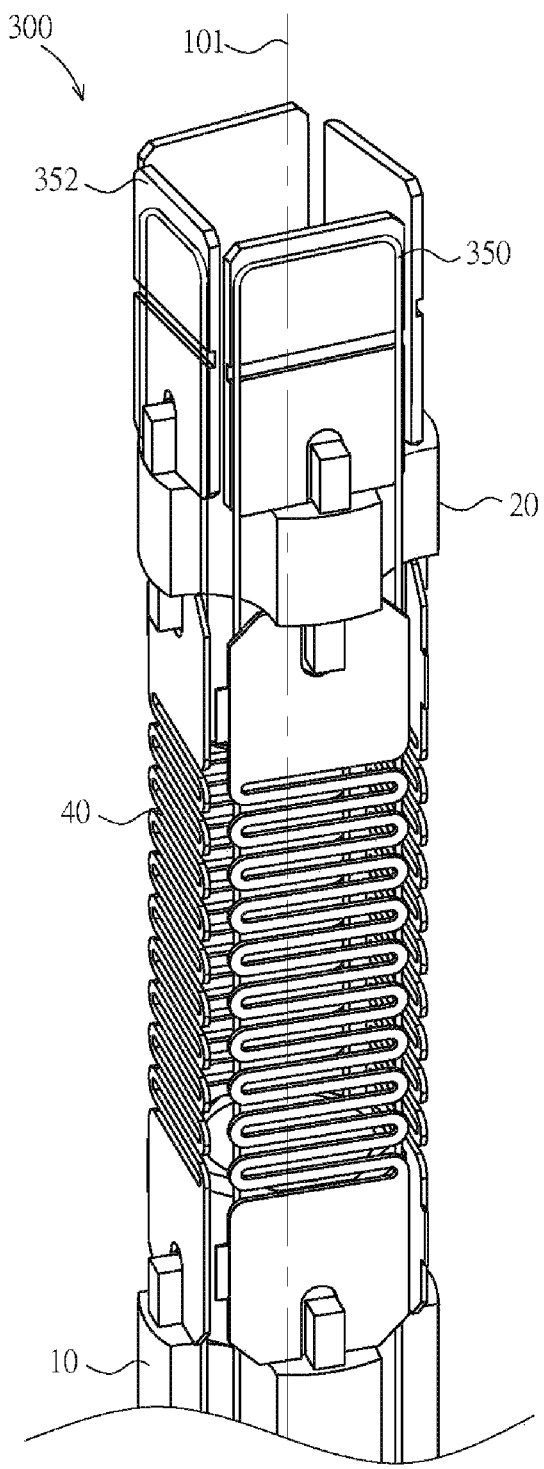
FIG. 8 is an enlarged schematic view showing a portion of the deflection device of steerable endoscope according to a third embodiment of the invention.

In addition, the above embodiment is described by taking the operation of a single elastic reposition member 40 corresponding to two second terminal components 52 as an example, while the operation of the single elastic reposition member 40 of the present invention can also correspond to only one second terminal component 52 or only one first terminal component 51. Please refer to FIG. 8, as well as FIGS. 2 and 3. FIG. 8 shows an enlarged schematic diagram of the components of the deflection device of steerable endoscope 300 of the third good embodiment of the present invention. As shown in FIG. 8, the deflection device of steerable endoscope 300 includes a first base 10, a second base 20, four elastic reposition members 40, four tendon wires 350, four second terminal components 352 and four first terminal components 51 (Please refer to FIGS. 2 and 3 for the position of the first terminal components 51).

The major difference between the third embodiment and the above embodiments is that each second terminal component 352 of the third embodiment is located right above each elastic reposition member 40, and each tendon wire 350 extends upward from the first terminal component 51 of the first base 10, spans and links to the second terminal component 352 of the second base 20, and then extends downward to another first terminal component 51 of the first base 10. That is, each tendon wire 350 surrounds three edges of each elastic reposition member 40 with a ⊓-shape.

Hereby, when operating the deflection device of steerable endoscope 300, the control unit 60 of FIG. 1 applies current to the two first terminal components 51 on both sides of the corresponding elastic reposition member 40 (voltage may not be applied to the second terminal components 352), the single U-shape (or inverted U-shape) tendon wire 350 corresponding to the above elastic reposition member 40 generates a contraction force due to the received current, and the contraction of the tendon wire 350 drives the second base 20 and the second terminal component 352 to bend toward the elastic reposition member 40.

When operating the deflection device of steerable endoscope 300, the power source including current or voltage need not apply to the second terminal components 352, so the control unit 60 of FIG. 1 need not electrically connect to the second terminal components 352, which further simplifies the connection and control of the circuit structure, as well as the components of the deflection device of steerable endoscope 300, and improves the mechanical reliability. Furthermore, because the control unit 60 of FIG. 1 can control the bending of the elastic reposition member 40 only by controlling the currents of the two first terminal components 51, the operation process can be simplified. In addition, since the currents on the two opposite side of the single elastic reposition member 40 are essentially the same, the bending direction of the four elastic reposition members 40 can be controlled more accurately.

In other embodiments, the above U-shape (or inverted U-shape) tendon wires 350 may be replaced by two linear-type tendon wires 50. Each second terminal component 352 is electrically linked and fixed to two tendon wires 50, which are respectively electrically connected and fixed downward to two first terminal components 51. Thus, the deflection device of steerable endoscope 300 includes eight tendon wires 350. Besides, the first terminal components 51 and the second terminal components 52 and 352 can be omitted in the present invention. That is, integrate the structure and function of the first terminal components 51 and the second terminal components 52 and 352 onto the first base 10, the second base 20 and the third base 30, so as to further simplify the structure. The tendon wires 50 and 350 described in the previous embodiment are located on the outside the first terminal components 51 and the second terminal components 52 and 352 (but not limited to that). The tendon wires 50 and 350 of the present invention may also be positioned on the inner side the first terminal components 51 and the second terminal components 52 and 352.

As mentioned above, the deflection device of steerable endoscope adopts elastic reposition members with a waveform bars and shape memory alloy tendon wires to drive the steering. It can precisely control the bending operation of endoscope, simplify the structure of deflection device, apply to small-size endoscope, and reduce the manufacturing cost.

Even though numerous characteristics and advantages of certain inventive embodiments have been set out in the foregoing description, together with details of the structures and functions of the embodiments, the disclosure is illustrative only. Changes may be made in detail, especially in matters of arrangement of parts, within the principles of the present disclosure to the full extent indicated by the broad general meaning of the terms in which the appended claims are expressed.

What is claimed is:

1. A deflection device of steerable endoscope, comprising:
   a first base, which has a plurality of first clamp parts;
   a second base, which is positioned distally to the first base along a direction of an endoscope central axis and has a plurality of second clamp parts;
   a plurality of elastic reposition members, which are inlaid between the first base and the second base, and each elastic reposition member comprising:
      a first plate, which is connected to the first base and has a third clamp part;
      a second plate, which is connected to the second base and has a fourth clamp part; and
      a waveform bar, which is connected between the first plate and the second plate, a wave-height direction of the waveform bar is not parallel to the direction of the central axis of the endoscope; and
   a plurality of tendon wires, which are arranged on opposite sides of each elastic reposition member and the length direction of the tendon wire is along the endoscope central axis and maintains a distance from the endoscope central axis;
   wherein the third clamp part cooperates with one of the first clamp parts by the cooperation of a groove and rib configuration to connect the first plate to the first base while the fourth clamp part cooperates with one of the second clamp parts by the cooperation of a groove and rib configuration to connect the second plate to the second base.

2. The deflection device of steerable endoscope of claim 1, wherein the first clamp parts and the second clamp parts have a plurality protruding ribs and the third clamp parts and the fourth clamp parts have a plurality of grooves cooperated with the protruding ribs.

3. The deflection device of steerable endoscope of claim 1, wherein the wave-height direction of each waveform bar is virtually perpendicular to the direction of the endoscope central axis.

4. The deflection device of steerable endoscope of claim 1, wherein the tendon wires include shape memory alloy.

5. The deflection device of steerable endoscope of claim 4 further comprises a control unit, which has a power generator and is electrically connected to the tendon wires, the power generator being generating current to the each of the tendon wires to control contraction and stretch of the tendon wires, respectively.

6. The deflection device of steerable endoscope of claim 4, further comprising:
   a plurality of first terminal components, which are connected to the first base; and
   a plurality of second terminal components, which are connected to the second base,
   wherein two ends of each tendon wires are respectively fixed and electrically connected to the first terminal component and the second terminal component.

7. The deflection device of steerable endoscope of claim 1, further comprising:
   a third base is located above the second base along the direction of the endoscope central axis,
   wherein a part of the elastic reposition members are embedded between the second base and the third base, while the other part of the elastic reposition members are embedded between the first base and the second base.

8. The deflection device of steerable endoscope of claim 7, further comprising:
   a plurality of first terminal components are connected to the first base; and
   a plurality of second terminal components are connected to the third base,
   wherein the tendon wires extend upward from the first base, across the second base, and to the third base, and the tendon wires are respectively fixed and electrically connected to the first terminal component and the second terminal component.

9. The deflection device of steerable endoscope of claim 7, wherein each second terminal component is electrically connected to the tendon wires.

* * * * *